United States Patent
Reddy et al.

(10) Patent No.: US 10,901,058 B2
(45) Date of Patent: Jan. 26, 2021

(54) CHEMICAL EXCHANGE SATURATION TRANSFER (CEST) IMAGING OF LACTATE (LATEST)

(71) Applicant: The Trustees Of The University Of Pennsylvania, Philadelphia, PA (US)

(72) Inventors: Ravinder Reddy, Gladwyne, PA (US); Hari Hariharan, Mount Laurel, NJ (US); Catherine DeBrosse, Norristown, PA (US); Ravi Prakash Reddy Nanga, Secane, PA (US); Puneet Bagga, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 445 days.

(21) Appl. No.: 15/424,344

(22) Filed: Feb. 3, 2017

(65) Prior Publication Data

US 2017/0227619 A1    Aug. 10, 2017

Related U.S. Application Data

(60) Provisional application No. 62/291,586, filed on Feb. 5, 2016.

(51) Int. Cl.
*G01R 33/56* (2006.01)
*A61B 5/055* (2006.01)
(Continued)

(52) U.S. Cl.
CPC .......... *G01R 33/5601* (2013.01); *A61B 5/055* (2013.01); *A61B 5/14546* (2013.01);
(Continued)

(58) Field of Classification Search
CPC ............ G01R 33/5601; G01R 33/5605; G01R 33/5659; G01R 33/56563; A61B 5/14546;
(Continued)

(56) References Cited

U.S. PATENT DOCUMENTS 5,121,059 A    6/1992   Wieland
6,963,769 B1   11/2005  Balaban et al.
(Continued)

FOREIGN PATENT DOCUMENTS

WO    2008/020765 A2    2/2008

OTHER PUBLICATIONS

Weinstein, EA et al., Imaging Enterobacteriaceae infection in vivo with 18F-fluorodeoxysorbitol positron emission tomography. Science Translational Medicine, Oct. 22, 2014; p. 10.
(Continued)

*Primary Examiner* — Catherine M Voorhees
(74) *Attorney, Agent, or Firm* — BakerHostetler

(57) ABSTRACT

CEST imaging technique and MR scanning are used as an MRI method for detecting levels of lactate in vivo by exploiting the exchange of —OH protons on lactate with bulk water. In accordance with this method, one first obtains a lactate CEST MRI map of a slice of the body of a patient. A contrast agent such as pyruvate, glucose or glutamine is administered and a post-administration CEST MRI map is obtained. The difference in the spatial maps indicates the level of expression of lactate in the tissue of interest.

17 Claims, 8 Drawing Sheets

(51) Int. Cl.

| | |
|---|---|
| *A61B 5/00* | (2006.01) |
| *A61K 49/10* | (2006.01) |
| *A61K 9/00* | (2006.01) |
| *A61B 5/145* | (2006.01) |
| *G01R 33/565* | (2006.01) |

(52) U.S. Cl.
CPC .......... *A61B 5/4848* (2013.01); *A61K 9/0019* (2013.01); *A61K 49/10* (2013.01); *G01R 33/5605* (2013.01); *G01R 33/5659* (2013.01); *G01R 33/56563* (2013.01)

(58) Field of Classification Search
CPC .... A61B 5/055; A61B 5/4848; A61K 9/0019; A61K 49/10
See application file for complete search history.

(56) References Cited

U.S. PATENT DOCUMENTS

| | | | |
|---|---|---|---|
| 8,278,925 B2 | 10/2012 | Sun et al. | |
| 8,686,727 B2 | 4/2014 | Reddy et al. | |
| 9,157,976 B2 | 10/2015 | Reddy et al. | |
| 2005/0059881 A1* | 3/2005 | Balaban | A61B 5/055 600/420 |
| 2006/0051480 A1 | 3/2006 | Miles | |
| 2012/0019245 A1* | 1/2012 | Reddy | G01R 33/5601 324/309 |
| 2014/0142180 A1* | 5/2014 | Birsoy | G01N 33/574 514/557 |
| 2014/0154185 A1* | 6/2014 | Van Zijl | A61B 5/055 424/9.35 |
| 2014/0213887 A1* | 7/2014 | Reddy | G01R 33/5605 600/414 |
| 2014/0288411 A1* | 9/2014 | Shapiro | A61K 49/1809 600/420 |
| 2015/0086484 A1* | 3/2015 | Hanes | A61K 9/1271 424/9.3 |
| 2016/0081578 A1* | 3/2016 | Gazit | A61B 5/055 600/410 |

OTHER PUBLICATIONS

Walker-Samuel, S et al., In vivo imaging of glucose uptake and metabolism in tumors. Nature Medicine, Aug. 2013; pp. 4, 8, 12.

Nasrallah, F et al., Imaging brain deoxyglucose uptake and metabolism by glucoCEST MRI. Journal of Cerebral Blood Flow and Metabolism. May 15, 2013; pp. 1271, 1273.

Kogan, et al. Method for high-resolution imaging of creatine in vivo using chemical exchange saturation transfer. Magn. Reson. Med. 71, 164-72 (2013).

Kogan, Chemical Exchange Saturation Transfer (CEST) Imaging: Description of Technique and Potential Clinical Applications, Current Radiology Reports, 1(2): 102-114, Jun. 1, 2013.

Greenwood, J et al., Hyperosmolar opening of the blood brain barrier in the energy depleted rat brain. Part 1. Permeability studies: Cerebral Blood Flow and Metabolism; Feb. 1988; title, abstract.

Cai, Magnetic Resonance Imaging of Glutamate, Nature Medicine, 2012, 18, 302-306.

Barney, BM et al., A Pilot Study Comparing FLT-PET and FDG-PET in the Evaluation of Response to Cetuximab and Radiation Therapy in Advanced Head and Neck Malignancies. Nuclear Medicine and Radiation Therapy. Feb. 5, 2012; title, pp. 1-3.

Testa, et al., Prodrugs Revisited: The "Ad Hoc" Approach as a Complement to Ligand Design. Medicinal Research Reviews, 16(3):233-241.

Alauddin, Positron emission tomography (PET) imaging with 18F-based radiotracers. American Journal of Nuclear Medicine and Molecular Imaging, 2012, 2(1):55-76.

DeBrosse et al., "Lactate Chemical Exchange Saturation Transfer (LATEST) Imaging in vivo a Biomarker for LDH Activity", Scientific Reports, Jan. 22, 2016, 1-9.

Cheng et al., "Impact of carbohydrate restriction with and without fatty acid loading on myocardial 18F-FDG uptake during PET:A randomized controlled trial", J. Nucl. Cardiol, 2010, 286-291.

Arrieta, M.C., et al., "Alterations in Intestinal Permeability", Gut, pp. 1512-1520 (Year: 2005).

Bornemann, V., et al., "Intestinal Metabolism and Bioaccumulation of Sucralose in Adipose Tissue in the Rat", J. Tox. Env. Health, Part A., pp. 913-923 (Year: 2018).

\* cited by examiner

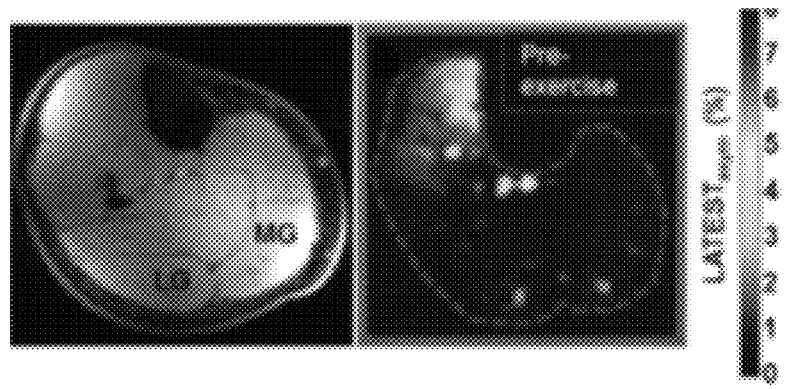
FIG. 4A    FIG. 4B
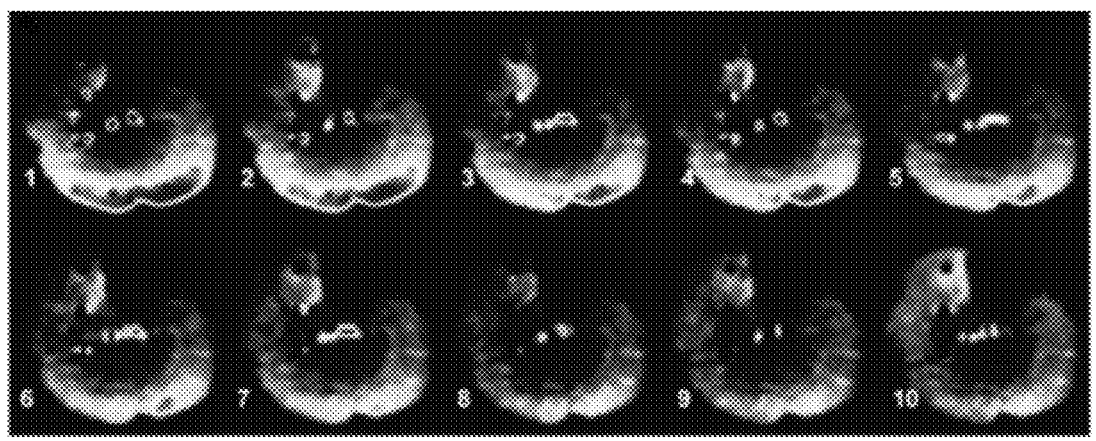
FIG. 4C
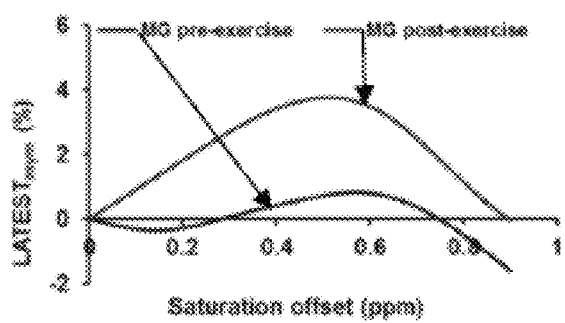 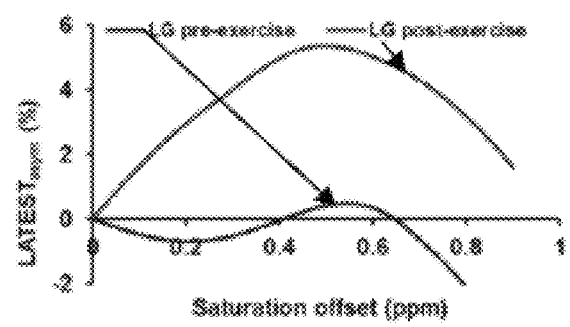
FIG. 4D    FIG. 4E

CHEMICAL EXCHANGE SATURATION TRANSFER (CEST) IMAGING OF LACTATE (LATEST)

CROSS-REFERENCE TO RELATED APPLICATION

This application claims priority to U.S. Provisional Patent Application No. 62/291,586, filed Feb. 5, 2016, the entirety of which is incorporated by reference for any and all purposes.

GOVERNMENT RIGHTS

This invention was made with government support under grant number P41 EB015893 and R01NS087516 awarded by the National Institutes of Health. The government has certain rights in the invention.

TECHNICAL FIELD

This invention relates generally to the use of a magnetic resonance imaging (MRI) method based on lactate chemical exchange saturation transfer (CEST) to image lactate (LATEST). The LATEST method exploits the exchange of lactate hydroxyl protons with bulk water.

BACKGROUND

MRI is a non-invasive imaging technique that provides images with soft tissue contrast. MR imaging contrast of biological tissues is generally based on the relaxation properties of water protons, which usually reflect a combination of spin-spin ($T_2$) and spin-lattice ($T_1$) relaxation. MRI detects the signal from bulk protons in biological tissues as they have long $T_2$ relaxation.

The CEST imaging technique, which provides an indirect way of detecting the signal from exchangeable protons with bulk water, is described in U.S. Pat. Nos. 8,686,727 and 9,157,976, incorporated herein by reference. To date, there are no reports of using the CEST imaging technique to image the hydroxyl protons of lactate in vivo. Changes in lactate metabolism are associated with a wide variety of diseases including cancer, cardiac failure, liver disease, diabetes mellitus, and neurological disorders such as epilepsy. Even in the presence of sufficient oxygen, tumor cells derive their energy from glycolysis (the Warburg effect), which leads to increased production of lactic acid. Many studies have shown that tumor lactate levels correlate with increased metastasis, tumor recurrence, and poor outcomes. Lactate also plays a role in promoting tumor inflammation and can function as a signaling molecule that stimulates tumor angiogenesis. Thus, non-invasive measurement of lactate is of tremendous significance to the study of metabolic defects in a wide range of pathologies.

Magnetic resonance spectroscopy (MRS), which employs both $^1H$ and $^{13}C$, has been used to measure lactate levels in vivo both statically and dynamically. A method for measuring lactate in vivo using MRS is disclosed in U.S. Pat. No. 5,121,059. However, MRS is limited by inadequate sensitivity and spatial resolution.

A second method for imaging lactate in vivo involves $^{13}C$-labeled pyruvate infusion and dynamic nuclear polarization (DNP), which provides greater than 10,000 fold signal enhancement compared to conventional MRS. DNP-based imaging of hyperpolarized 1-$^{13}C$ pyruvate may enable observation of cellular bioenergetics such as glycolysis, the citric acid cycle, and fatty acid synthesis. Conversion of $^{13}C$ pyruvate to $^{13}C$ lactate and $^{13}C$ alanine has been studied extensively in vivo in animal models. In those studies, injection of $^{13}C$ pyruvate enables dynamic imaging of lactate and alanine. A method for monitoring conversion of hyperpolarized $^{13}C$-pyruvate into $^{13}C$-lactate over time is disclosed in WO-2008/020765. Despite its high sensitivity, imaging of DNP-based hyperpolarized pyruvate and lactate presents several challenges, precluding its widespread utility in a clinical setting: (1) it requires ≥100 mM of $^{13}C$-enriched-pyruvate, which is quite expensive; (2) it requires an onsite DNP polarizer; (3) it requires complex modeling to analyze the data given that the metabolites lose polarization due to both $T_1$ decay and ongoing metabolism; and (4) it only probes fast kinetics (<1 min) of lactate turnover from $^{13}C$-labeled pyruvate.

Accordingly, there is a need for non-invasive methods of measuring lactate levels in-vivo, capable of capturing extended kinetics of lactate metabolism.

SUMMARY

In some embodiments, MRI methods are provided and comprise (i) applying a Chemical Exchange Saturation Transfer (CEST) saturation pulse train to a patient at a range of frequency offsets around a frequency of exchangeable protons of lactate as well as the same frequency offsets on the opposite of the water resonance; (ii) acquiring a magnetic resonance (MR) image of a slice of the body of said patient to which the CEST saturation pulse has been applied in order to obtain an initial lactate CEST MRI map; (iii) administering an effective amount of a contrast agent to said patient; (iv) acquiring a second MR image of said slice of the body of said patient to which the CEST saturation pulse has been applied to obtain a second lactate CEST MRI map; and (v) determining a CEST contrast image by taking a ratio of a difference image obtained by subtraction of saturation images obtained during said MR imaging steps with saturation applied at both positive and negative frequencies with respect to water resonance and an image with no saturation.

In other embodiments, methods of monitoring the effectiveness of a pharmaceutical agent in treating a condition in a patient are provided and comprise (i) applying a CEST saturation pulse train to a patient at a range of frequency offsets around a frequency of exchangeable protons of lactate as well as the same frequency offsets on the opposite of the water resonance; (ii) acquiring a MR image of a slice of the body of said patient to which the CEST saturation pulse has been applied in order to obtain an initial lactate CEST MRI map; (iii) administering a pharmaceutical agent to said patient; (iv) administering an effective amount of a contrast agent to said patient; (v) acquiring a second MR image of said slice of the body of said patient to which the CEST saturation pulse has been applied to obtain a second lactate CEST MRI map; and (vi) determining a CEST contrast image by taking a ratio of a difference image obtained by subtraction of saturation images obtained during said MR imaging steps with saturation applied at both positive and negative frequencies with respect to water resonance and an image with no saturation.

In further embodiments, methods of distinguishing abnormal tissue from normal tissue in a patent are provided and comprise (i) applying to a suspected abnormal tissue a CEST saturation pulse train at a range of frequency offsets around a frequency of exchangeable protons of lactate as well as the same frequency offsets on the opposite of the water resonance; (ii) acquiring a magnetic resonance (MR) image of a said suspected abnormal tissue to which the CEST saturation pulse has been applied in order to obtain an initial lactate CEST MRI map; (iii) administering an effective amount of a contrast agent to said patient; (iv) acquiring a second MR image of said suspected abnormal tissue to which the CEST saturation pulse has been applied to obtain a second lactate CEST MRI map of the area of the suspected abnormal tissue; and (v) determining a CEST contrast image by taking a ratio of a difference image obtained by subtraction of saturation images obtained during said MR imaging steps with saturation applied at both positive and negative frequencies with respect to water resonance and an image with no saturation.

Other aspects and embodiments of the invention will be readily apparent from the following detailed description of the invention.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific compositions, methods, devices, and systems disclosed. In addition, the drawings are not necessarily drawn to scale.

FIG. 3A, FIG. 3B and FIG. 3C are anatomical image from three animals, with flank tumor region indicated by dotted red line. FIG. 3D, FIG. 3E and FIG. 3F are the corresponding pre-infusion LATEST maps, and FIG. 3G, FIG. 3H and FIG. 3I are the corresponding post-infusion LATEST maps.

FIG. 4A is an anatomical image of human calf muscle. FIG. 4B is a pre-exercise, resting-state CEST map showing ~1% $LATEST_{asym}$ at 0.5 ppm. FIG. 4C shows ten post-exercise images acquired over 18 minutes after 3 minutes of exhaustive exercise, wherein the first image (1), obtained 3 minutes after cessation of exercise, shows a CEST asymmetry increase in the medial gastrocnemius (MG) and lateral gastrocnemius (LG) muscles of ~4-6%, and wherein each of the subsequent images (2-10), acquired with a resolution of 1.8 minutes, shows lactate recovery in the MG and LG. All LATEST images were acquired using $B_{1rms}$=1.73 µT and 3 s duration. FIG. 4D and FIG. 4E are asymmetry plots, corrected for $B_0$ and $B_1$, for pre- and post-exercise LATEST of the (FIG. 4D) MG and (FIG. 4E) LG muscles from a representative subject, acquired with $B_{1rms}$=0.73 µT, 3 s duration.

FIG. 6A is a $B_0$ (WASSR) map, acquired with $B_{1rms}$=0.29 µT and 200 ms duration, collected from 0 ppm to ±0.5 ppm, in steps of 0.05 ppm. FIG. 6B is a $B_1$ GRE map for human calf muscle, (FIG. 6C-FIG. 6E, top row) pre (FIG. 6C-FIG. 6E, bottom row) and post-infusion $B_0$ and $B_1$ maps for three animals with flank tumors. The $B_0$ map is identical for pre- and post-infusion. No center frequency change, no animal movement.

FIG. 7A shows a Z-spectrum for the MG muscle region pre-exercise and-a Z-spectrum for the MG muscle region post-exercise. FIG. 7B shows Z-spectra for the LG muscle region pre- and post-exercise. FIG. 7C shows Z-spectra from the tumor region in a representative animal pre- and post-infusion.

FIG. 8A shows $T_2$ maps overlaid on the anatomical image before exercise. FIG. 8B shows $T_2$ maps post-exercise, acquired with the same time resolution as the LATEST images. FIG. 8C plots the $T_2$ value in ms vs. recovery time in minutes.

DETAILED DESCRIPTION OF ILLUSTRATIVE EMBODIMENTS

Figure 1A:
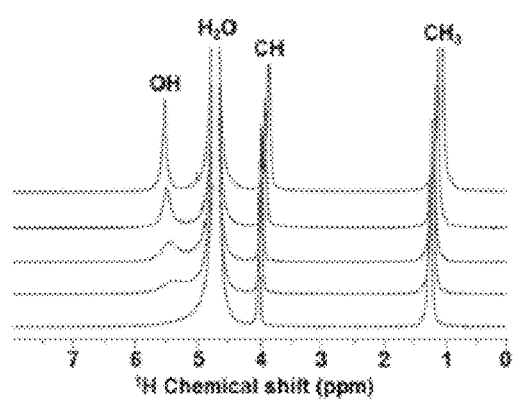
FIG. 1A depicts high-resolution NMR spectra of 15M sodium lactate in PBS buffer at pH 7.1±0.1) at varying temperatures acquired with Bruker Avance DMX 400 MHz spectrometer equipped with a 5 mm PABBI proton probe.

The inventors have exploited the exchange between lactate hydroxyl protons and bulk water protons to achieve high spatial resolution in vivo lactate CEST imaging. Those skilled in the art will appreciate that such methods may be repeated as needed as they do not involve any radioactive ligands or costly hyperpolarization methods. Also, lactate CEST imaging has been shown to have overs two orders of magnitude higher sensitivity compared to conventional MR spectroscopy. The methods may be performed in vivo or ex vivo as preferred by those skilled in the art.

In the present disclosure the singular forms "a", "an" and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" or "substantially" it will be understood that the particular value forms another embodiment. In general, use of the term "about" or "substantially" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about" or "substantially". In other cases, the gradations used in a series of values may be used to determine the intended range available to the term "about" or "substantially" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

The terms "patient" or "subject" as used herein are interchangeable and refer to a mammalian animal. In one embodiment, the patient or subject is a human. In another embodiment, the patient or subject is a veterinary or farm animal, a domestic animal or pet, or animal normally used for clinical research.

The methods described herein utilize CEST MRI techniques known in the art. See, e.g., Cai, Nature Medicine, 18, 302, 2012; Kogan, Current Radiology Reports, 1(2): 102-114, Jun. 1, 2013; and U.S. Pat. Nos. 8,686,727 and 9,157,976, which are incorporated herein by reference.

Obtaining an initial lactate CEST MRI map comprises (i) applying a CEST saturation pulse train and (ii) acquiring an MR image of a slice of the body of the patient to which the CEST saturation pulse has been applied. The basic pulse sequence used in the CEST technique comprises two building blocks: (i) a highly frequency selective variable duration saturation pulse train with a number of identical shaped RF pulses and short delays and (ii) a set of RF spoiled GRE acquisition segments. For the CEST saturation building block, saturation pulse frequency offset, the total duration of the saturation pulse train, the individual duration of the pulses in the train, the RF duty cycle of the pulse train, and two choices for shapes of the individual RF pulses (Rectangle or Hanning windowed rectangle), all may be chosen by the user. For the acquisition building block, the RF flip angle, acquisition bandwidth, FOV, image matrix size and the number of shots to use to collect one image also may be chosen by the user. The number of segments per shot are calculated as image matrix size divided by the number of shots. Because CEST imaging of lactate exploits the exchange of the —OH protons on lactate with bulk water, CEST contrast may be improved by adjusting the amplitude and duration of the CEST saturation pulse train based on the proton exchange rate of lactate.

Due to the presence of —OH groups from other endogenous molecules (glucose, glycogen, etc.) it is possible that the baseline, endogenous LATEST signal may have contributions from these molecules. However, —OH groups from glucose and glycogen have resonances at around 1 ppm as opposed to ~0.4 ppm in the case of lactate. Other metabolites that may be present in tumors, such as pyruvate, do not have exchangeable hydroxyl protons, and would not be expected to contribute to the LATEST signal at 0.4 ppm. In skeletal muscle, possible contribution of creatine to the LATEST signal should be considered. Creatine CEST (CrCEST) experiments by Kogan et al. (Method for high-resolution imaging of creatine in vivo using chemical exchange saturation transfer. Magn. Reson. Med. 71, 164-72 (2013)), demonstrate that the guanidine protons of creatine resonate farther downfield at 1.8 ppm from bulk water, and require a much shorter saturation pulse (500 ms) and higher $B_1$ power of 2.9 μT. Furthermore, if creatine contributed to the LATEST effect at ~0.5 ppm, higher signals in the resting state skeletal muscle would be observed. Additionally, increased post-exercise creatine has been shown to recover within ~2 minutes, which is much shorter than the ~18 minutes it takes for the LATEST signal to dissipate post-exercise. Based on in vivo asymmetry plots presented in FIG. 4 and the intercept in FIG. 5D, the contributions to LATEST from other metabolites are small with the given saturation parameters After the initial lactate CEST MRI map is obtained, an effective amount of a contrast agent may be administered to the patient. It is further contemplated that the contrast agent be pyruvate, glucose, glutamine or a combination thereof. One of skill in the art would appreciate that increased glucose utilization in tumor cells is due, to a certain extent, to PI3K/Akt/mTOR-mediated up-regulation of glucose transporters. Even in the presence of sufficient oxygen, tumor cells derive their energy from the metabolic breakdown of glucose (glycolysis), which leads to increased production of lactic acid. Tumor cells are also known to derive energy from glutamine, which may be converted to pyruvate and then to lactate in a process termed glutaminolysis. Many clinical studies have shown that high lactate levels (>8 mmol/L) are associated with the subsequent development of metastases. Such tumors include primary cervical, head and neck, and rectal cancers. In cancer patients, serum total lactate dehydrogenase (LDH) levels are often increased, and the gene for LDH-A protein is up regulated in tumors. These features have been linked to poor prognosis, and a greater metastatic potential has been reported in patients with high LDH serum levels. Furthermore, LDH-A protein is required for the maintenance and progression of many tumors. Specifically, LDH catalyzes the interconversion of pyruvate and lactate with simultaneous conversion of NADH and $NAD^+$. When oxygen is absent or in short supply, it converts pyruvate to lactate, and it performs the reverse reaction during the lactic acid cycle in the liver. Using LATEST imaging techniques, it is possible to investigate tumor metabolism through injection of non-enriched pyruvate, glucose or glutamine. Moreover, administration of non-enriched pyruvate, glucose and/or glutamine may act as a contrast agent insofar as administration of excess pyruvate, glucose and/or glutamine may result in an increase in lactate in those cells primarily deriving their energy from glycolysis or glutaminolysis.

An effective amount of a contrast agent is administered to the patient. The term "effective amount" as used herein refers to a non-toxic amount of the contrast agent. The effective amount will depend on the type of contrast agent, patient's age, weight, height, or the like, unrelated or related medical conditions afflicted by the patient, condition being treated, among others. In some embodiments, the effective amount of contrast agent is that which may be safely administered to the patient. In other embodiments, the effective amount of the contrast agent is that set forth by the FDA. In some embodiments, the contrast agent is pyruvate, which may be in the form of organic salts, e.g., calcium or sodium salts of pyruvic acid; or esters of pyruvic acid such as ethyl amino pyruvate. In other embodiments, the contrast agent is glucose, which may also be referred to as dextrose. In still other embodiments, the contrast agent is glutamine, which may be in the form of L-glutamine. In further embodiments, the contrast agent is a combination of pyruvate, glucose and glutamine.

The contrast agent may be administered by any permitted and approved means. In some embodiments, the contrast agent is administered orally, nasally, transdermally, intravenously, subcutaneously, intramuscularly, intra-arterially, intraperitoneally, intracavitary, epiduraly, or by infusion. In other embodiments, the contrast agent is administered as a single dose. In further embodiments, the contrast agent is administered as two or more doses. In still other embodiments, the contrast agent is administered over a period of time such as by infusion. By administration via infusion, multiple CEST MRI images may be obtained while simultaneously keeping a level of contrast agent in the patient.

Although the contrast agent may be administered alone, it may also be administered in the presence of one or more pharmaceutical carriers that are physiologically compatible. The carriers may be in dry or liquid form and must be pharmaceutically acceptable. In some embodiments, the liquid pharmaceutical compositions are sterile solutions or suspensions.

When liquid carriers are utilized, they may be sterile liquids. Liquid carriers are typically utilized in preparing solutions, suspensions, emulsions, syrups and elixirs. In some embodiments, the contrast agent is dissolved a liquid carrier. In another embodiment, the contrast agent is suspended in a liquid carrier. One of skill in the art of formulations would be able to select a suitable liquid carrier, depending on the route of administration. In one embodiment, the liquid carrier includes, without limitation, water, organic solvents, oils, fats, or mixtures thereof. In another embodiment, the liquid carrier is water containing cellulose derivatives such as sodium carboxymethyl cellulose. In a further embodiment, the liquid carrier is water and/or dimethylsulfoxide. Examples of organic solvents include, without limitation, alcohols such as monohydric alcohols and polyhydric alcohols, e.g., glycols and their derivatives, among others. Examples of oils include, without limitation, fractionated coconut oil, arachis oil, corn oil, peanut oil, and sesame oil and oily esters such as ethyl oleate and isopropyl myristate.

Alternatively, the contrast agent may be formulated in a solid carrier. In one embodiment, the composition may be compacted into a unit dose form, i.e., tablet or caplet. In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, the solid carrier may also act as a flavoring agent, lubricant, solubilizer, suspending agent, filler, glidant, compression aid, binder, disintegrant, or encapsulating material. Suitable solid carriers include, without limitation, calcium phosphate, dicalcium phosphate, magnesium stearate, talc, starch, sugars (including, e.g., lactose and sucrose), cellulose (including, e.g., microcrystalline cellulose, methyl cellulose, sodium carboxymethyl cellulose), polyvinylpyrrolidine, low melting waxes, ion exchange resins, and kaolin. The solid carrier can contain other suitable excipients, including those described below.

Examples of excipients which may be combined with the contrast agent include, without limitation, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, syrups, thickening agents, or viscosity regulators. See, the excipients described in the "Handbook of Pharmaceutical Excipients", 5th Edition, Eds.: Rowe, Sheskey, and Owen, APhA Publications (Washington, D.C.), Dec. 14, 2005, which is incorporated herein by reference.

After administering an effective amount of a contrast agent, a second MR image of the slice of the body of the patient to which the CEST saturation pulse was applied is acquired to obtain a second lactate CEST MRI map. Subsequently, a CEST contrast image is determined by taking a ratio of a difference image obtained by subtraction of preferably $B_0$ and $B_1$ corrected saturation images obtained with saturation applied at both positive and negative frequencies with respect to water resonance and an image with no saturation.

Because LATEST imaging maps lactate via bulk water signal, it can provide high spatial resolution maps of lactate comparable to that of proton imaging. Furthermore, LATEST imaging contrast can be easily turned "on" and "off" by simply changing the imaging parameters and imaging post-processing is relatively simple. The direct subtraction of the two images with contrast "on" and "off" can provide reliable quantification of lactate levels.

The imaging methods described herein may be performed in conjunction with conventional MRI methods. The term "conventional MRI" as used herein refers to any type of MRI that does not include CEST. The conventional MRI technique may be utilized in neuroimaging, cardiovascular MRI, musculoskeletal MRI, liver MRI, gastrointestinal MRI, functional MRI and oncological identification. In some embodiments, the conventional PRI includes, without limitation, anatomic proton-density weight, $T_1$ weighted, $T_2$ weighted, angiography, functional MRI, or combinations thereof.

Conventional MRI may be performed prior to, concurrently with, or subsequent to the CEST MRI technique. When the CEST MRI methods are supplemented by conventional MRI, the conventional MRI images are obtained similarly. Specifically, a baseline conventional MRI image of the patient is obtained. After optional administration of the contrast agent, one or more conventional MRI images of the patient are then obtained. Comparison of the baseline conventional MRI image with the conventional MRI test image produces a final MRI image. In some embodiments, such comparisons with conventional MRI results provide complimentary information to the CEST MRI result.

The CEST contrast image and conventional MRI images, i.e., final images, may be displayed over time in a medium sensible to an operator. In some embodiments, the CEST contrast image is displayed as an indication of the level of expression of lactate. In some embodiments, a plurality of CEST contrast images is determined over a period of time. In further embodiments, the CEST contrast image is displayed as an indication of the level of expression of lactate over time.

This final image may then be analyzed by the operator, radiologist, attending physician, or any other medical professional. The final image provides a display of areas in the patient where lactate is expressed. In some embodiments, the lactate accumulates in abnormal tissues differently than in normal or healthy tissues. In other embodiments, the rate of accumulation of lactate in abnormal and normal or healthy tissue is calculated. In further embodiments, lactate accumulates in abnormal tissues at a different rate than in normal tissue.

Accumulation of lactate in abnormal tissue may depend on a number of factors including, without limitation, increased Pl3K-Akt/mTOR-mediated up-regulation of glucose transporters, increased reliance on glycosis as an energy source, and increased lactate dehydrogenase levels. Accordingly, the final image highlights any of these abnormal regions and may be useful in distinguishing abnormal tissue from normal tissue.

The term "abnormal" as used herein refers to tissue that is not indigenous to a subject. In some embodiments, the abnormal tissue includes, without limitation, neoplastic tissue, inflamed tissue, ischemic tissue, degenerated tissue, fibrotic tissue, among others, or combinations thereof. The neoplastic tissue may include any cancerous tissue type which may be visualized using CEST MRI. The abnormal tissue may be localized or spread out in different areas of the patient. In some embodiments, the abnormal tissue is a tumor.

Accordingly, a number of various types of cancers may be detected using the methods described herein. In some embodiments, the cancer is adrenal cancer, anal cancer, bile duct cancer, bladder cancer, bone cancer, brain cancer, breast cancer, pediatric cancer, Castleman disease, cervical cancer, colorectal cancer, endometrial cancer, esophageal cancer, Ewing family, eye cancer, gallbladder cancer, gastrointestinal cancer, gestational trophoblastic disease, Hodgkin disease, Kaposi sarcoma, kidney cancer, laryngeal and hypopharyngeal cancer, leukemia, liver cancer, lung cancer, lymphoma, malignant mesothelioma, multiple myeloma, myelodysplastic syndrome, nasal cavity and paranasal sinus cancer, nasopharyngeal cancer, neuroblastoma, Non-Hodgkin lymphoma, oral cavity and oropharyngeal cancer, osteosarcoma, ovarian cancer, pancreatic cancer, penile cancer, pituitary cancer, prostate cancer, retinoblastoma, rhabdomyosarcoma, salivary gland cancer, sarcoma, skin cancer, small intestine cancer, stomach cancer, testicular cancer, thymus cancer, thyroid cancer, uterine cancer, vaginal cancer, vulvar cancer, waldenstrom macroglobulinemia, and Wilms tumor.

A variety of degenerative, fibrotic, ischemic, and inflamed tissue types may be visualized using the methods described herein. In some embodiments, the degenerative, fibrotic, ischemic, or inflamed tissue may be specific to one region of the patient. In other embodiments, the degenerative tissue, fibrotic, ischemic, or inflamed is may be a result to injury, aging, disease or normal wear and tear. In further embodiments, the tissue type is damaged cartilage, infarcted heart tissue, and fibrotic liver tissue, among others.

Not only may the CEST MRI methods described herein be useful in pinpointing areas of abnormal tissue in a patient, but the methods may also be used in treatment therapies. Specifically, the CEST MRI methods described herein may be utilized to determine if a particular treatment therapy is effective. In some embodiments, the methods described herein may be used to determine if a method of treating abnormal tissue is effective, i.e., useful in reducing or ameliorating a condition in a patient. In other embodiments, the methods may be used in monitoring the effectiveness of a pharmaceutical agent, radiation, acupuncture, massage, physical therapy, among others, in treating the abnormal tissue. Accordingly, the methods described herein may, therefore, be effective in designing a therapy that effectively targets and treats the condition resulting in the abnormal tissue. The methods comprise the steps described herein including, without limitation, applying a CEST saturation pulse train at the desired frequency, acquiring a MR image of the slice of the body to which the CEST saturation pulse was applied, then administering a pharmaceutical agent to the patient. Thereafter, an effective amount of a contrast agent is administered to the patient, a second MR image of the slice of the body to which the CEST saturation pulse was applied is obtained, and a CEST contrast image is determined. One of skill in the art would be able to select a suitable timeframe, after administration of the pharmaceutical agent, for administering the contrast agent and obtaining test CEST MRI images.

"Treatment", or variations thereof, encompasses treatment of a subject clinically diagnosed as having a disease or medical condition. In one embodiment, the subject is treated and the disease or medical condition is eradicated, i.e., the subject is cured. As used herein, "prevention" encompasses prevention of symptoms in a subject who has been identified as at risk for the condition, but has not yet been diagnosed with the same and/or who has not yet presented any symptoms thereof.

The following Examples are provided to illustrate some of the concepts described within this disclosure. While each Example is considered to provide specific individual embodiments of composition, methods of preparation and use, none of the Examples should be considered to limit the more general embodiments described herein.

In the following Examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

EXAMPLES

Example 1

Phantom Studies

Figure 1B:
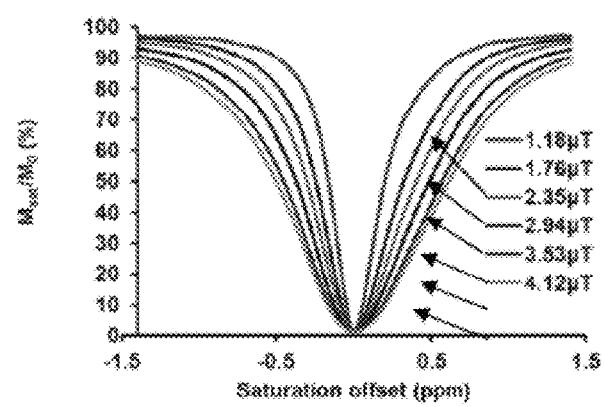
FIG. 1B and FIG. 1C depict Z-spectra and corresponding asymmetry plot of 50 mM lactate at 9.4 T, pH 7, at 37° C. with $B_{1rms}$ titrated from 1.18 µT-4.12 µT with a saturation duration of 5 s.
Figure 1C:
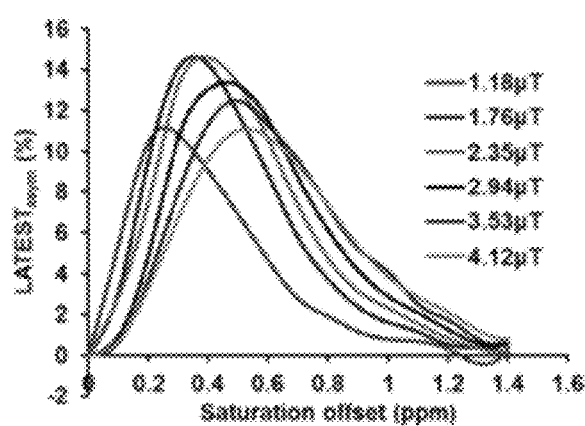
Figure 1D:
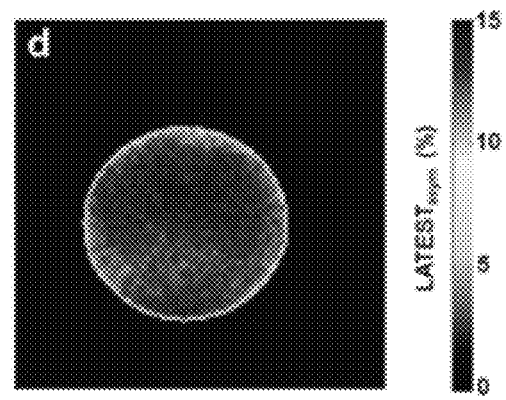
FIG. 1D is a CEST map for 50 mM lactate at 9.4 T, pH 7, at 37° C. with $B_{1rms}$ 2.35 µT, saturation duration 5 s.
Figure 2A:
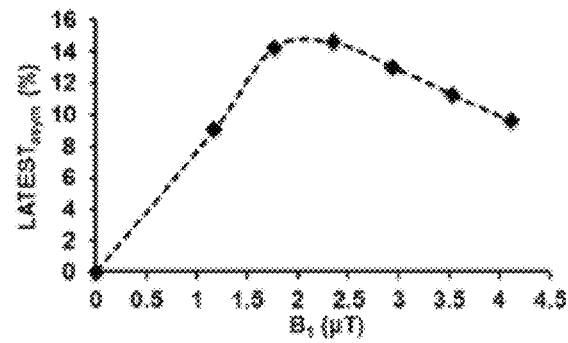
FIG. 2A depicts LATEST dependence on $B_1$ from a 50 mM lactate phantom at pH 7, at the saturation duration of 0.4 ppm offset from water.
Figure 2B:
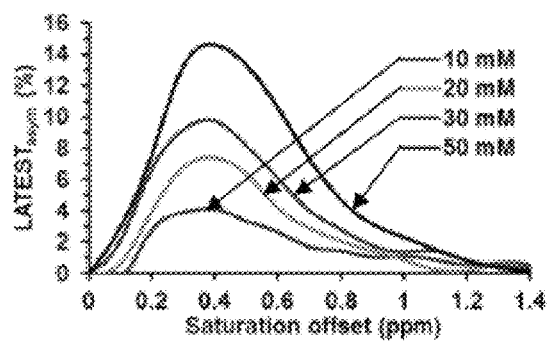
FIG. 2B is an asymmetry plot of LATEST at 10, 20, 30, and 50 mM lactate at pH 7, with $B_{1rms}$=2.35 µT and pulse duration=5 s.
Figure 2C:
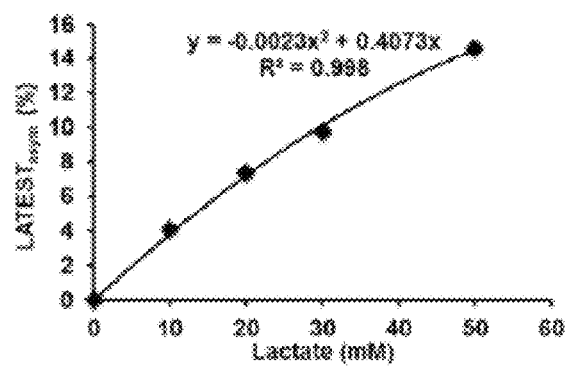
FIG. 2C is a concentration dependence plot of LATEST at 0.4 ppm, pH 7, with $B_{1rms}$=2.35 µT and pulse duration=5 s.
Figure 2D:
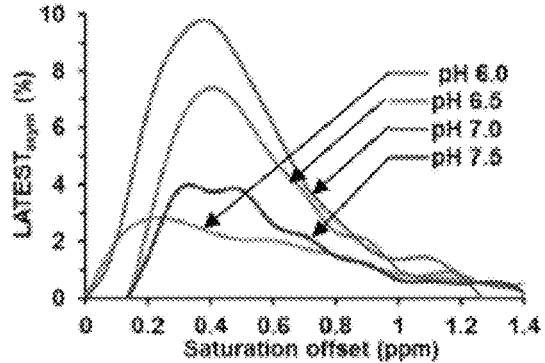
FIG. 2D is an asymmetry plot from 30 mM lactate, pH=6, 6.5, 7, and 7.5.
Figure 2E:
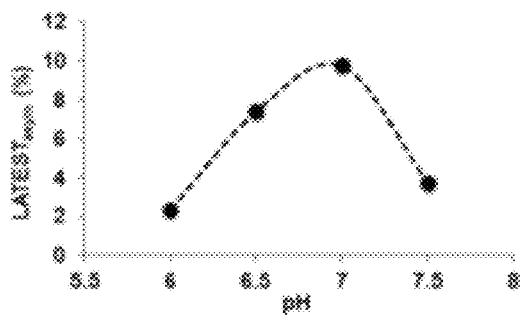
FIG. 2E is a plot of pH dependence of LATEST at 0.4 ppm from 30 mM lactate with $B_{1rms}$=2.35 µT, duration=5 s.

The chemical shift of the hydroxyl (—OH) proton resonance of sodium lactate, measured by 1D $^1$H NMR, varies from ~0.8 to 0.4 ppm offset from water as the temperature is changed from 4° C. to 27° C. At 37° C., the —OH resonance is not clearly visible by $^1$H NMR, owing to the significant exchange broadening and proximity to the water resonance (FIG. 1A). Consequently, the z-spectrum of 50 mM sodium lactate obtained at 9.4 T does not exhibit any sharp features at 37° C. (FIG. 1B). However, the CEST asymmetry plot of the same exhibits clear resonance centered between ~0.3 to 0.5 ppm (FIG. 1C). Typically, this peak is masked in the z-spectrum by the overwhelming water signal. In the asymmetry plot, the subtraction of the water signal elucidates the lactate —OH resonance at 0.4 ppm. A representative CEST map at 0.4 ppm of the 50 mM lactate phantom is shown in FIG. 1D. Optimal LATEST parameters in phantoms at 9.4 T were $B_{1rms}$=2.35 µT, with a 5 s duration (FIG. 2A). With the imaging parameters described, at neutral pH and 37° C., lactate exhibits ~0.4% CEST/mM at 9.4 T (FIGS. 2B and 2C). The pH dependence of 30 mM lactate at 9.4 T shows maximum LATEST signal at pH=7 (~10% LATEST asymmetry at 0.4 ppm downfield from water) (FIGS. 2D and 2E). At both lower and higher pH, a decrease in LATEST asymmetry at 0.4 ppm is observed.

At 7 T, the optimal parameters for LATEST in phantoms are: 5 s saturation length with ~1.09 µT $B_{1rms}$ at 25° C. and 1.46 µT $B_{1rms}$ at 37° C. With the imaging parameters described, at neutral pH and 25° C., lactate exhibits 0.25% CEST/mM at 7 T, with 1.09 µT ($B_{1rms}$). Based on the experimental signal-to-noise ratio (SNR), this method has sufficient sensitivity to detect 2 to 3 mM lactate.

The exchange rate (k) estimated from lactate phantoms (pH 7) at 25° C. is ~350±50$^{s-1}$ and at 37° C. is ~550±50$^{s-1}$. Therefore, the lactate chemical exchange rate is in the slow to intermediate condition and meets the requirement for observing the CEST effect for field strengths greater than 4 T.

Example 2

Animal Model Studies: LATEST Imaging of Lymphoma Flank Tumors

Figure 3J:
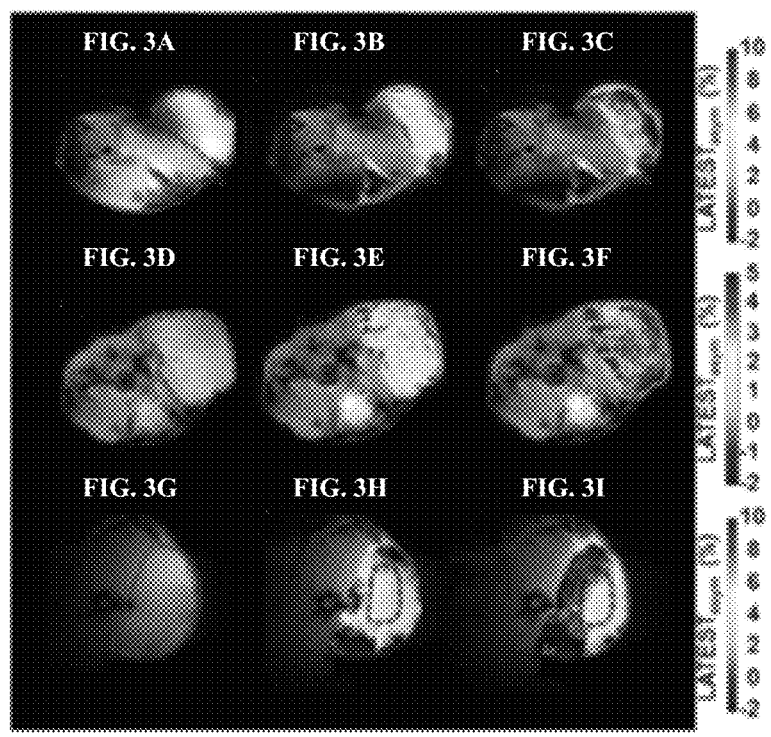
FIG. 3J is the corresponding asymmetry plot (asymmetry from Animal 3 in the third row is taken from region indicated in dotted black line).
Figure 3J:
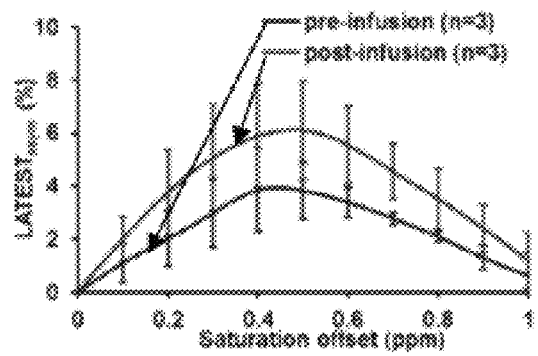
Figure 3K:
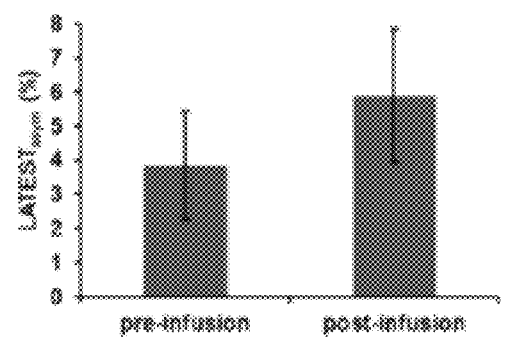
FIG. 3K is a graph of the LATEST change at 0.4 ppm from three animals pre- and post-infusion.

Anatomical images of flank tumors on three mice are shown in FIGS. 3A-3C. Baseline CEST maps from the tumor regions of each animal (FIGS. 3D-3F) show an average $LATEST_{asym}$ of ~3.5%. Following infusion of 300 mM pyruvate through the tail vein, the LATEST signal increased in the tumor regions (FIGS. 3G-3I). Average asymmetry plots from the tumor regions (FIG. 3J) showed an endogenous LATEST peak and subsequent increase post-infusion, centered ~0.5 ppm downfield from water. The asymmetry plot from one animal (row 3 of FIGS. 3A-3I) was obtained from the region of interest (ROI) indicated in the black dotted line (FIG. 3F). This region was used in order to avoid regions with large $B_0$ inhomogeneity, which was observed in the outer region of the tumor (FIG. 6). Data from lymphoma tumors of three animals showed a ~60% increase in LATEST asymmetry after ~40 minutes post-infusion of pyruvate (FIG. 3K).

Figure 3L:
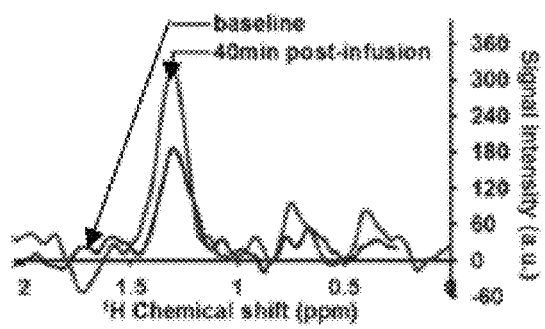
FIG. 3L is a plot of representative SEL-MQC $^1$H-MRS pre- and 40 minutes post-infusion from flank tumor.
Figure 3M:
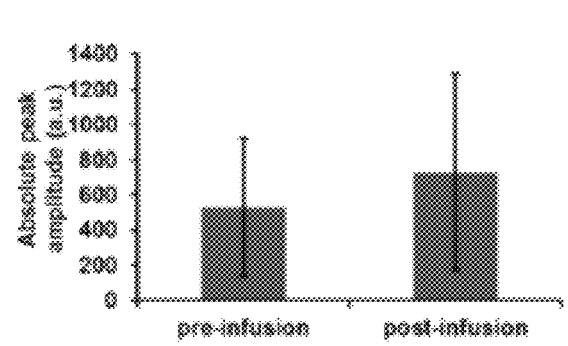
FIG. 3M is a graph of the increase in lactate peak amplitude from three animals (~40%) from spectroscopy.

In tumors, endogenous lactate levels are expected to be in the range of 2 to 10 mM[27]. Baseline LATEST observed in the tumor model is largely due to endogenous lactate, based on the ~0.4% LATEST asymmetry per mM of lactate observed in phantoms at 9.4 T. Tumor lactate was also measured in three animals with flank tumors, using SEL-MQC $^1$H MRS. Spectroscopy results pre- and post-infusion of pyruvate are shown for a representative animal (FIG. 3L). The increase in lactate peak amplitude after pyruvate infusion shown by spectroscopy (FIG. 3M) from three animals shows a trend in lactate change that is similar to the trend observed with LATEST.

Example 3

Human Studies: LATEST Imaging of Healthy Human Calf Muscle

Figure 5A:
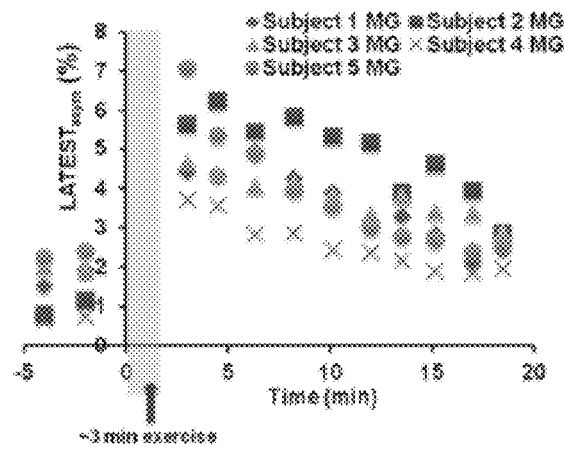
FIG. 5A is a plot of LATEST at 0.5 ppm in the medial gastrocnemius (MG) of resting-state calf muscle, and post-exercise recovery from 5 healthy volunteers.
Figure 5B:
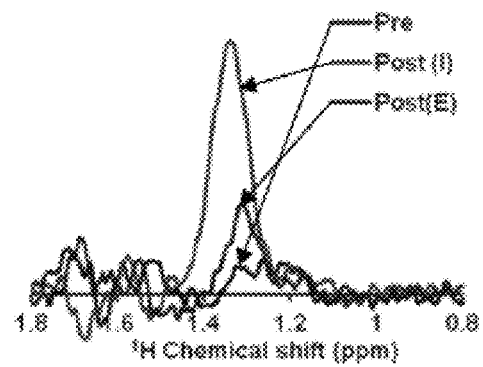
FIG. 5B is a plot of representative lactate MRS in a voxel from the MG/LG pre-exercise, immediately post-exercise, and after 20 minutes of recovery.
Figure 5C:
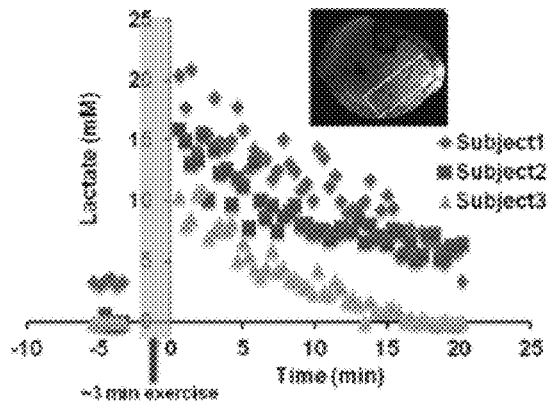
FIG. 5C shows pre- and post-exercise lactate edited MRS data from 3 healthy volunteers (representative voxel location from one subject shown in insert).
Figure 5D:
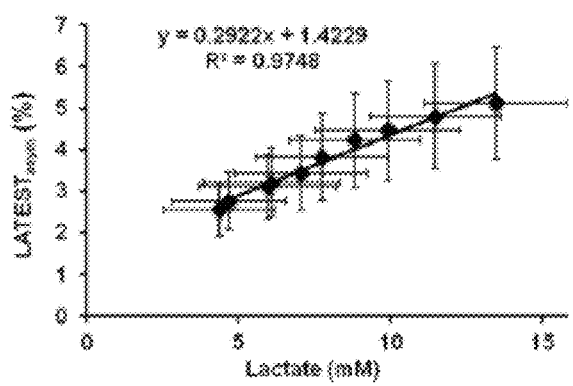
FIG. 5D is a plot of correlation of lactate concentration from spectroscopy and LATEST from the MG, wherein error bars indicate standard error.
Figure 6A:
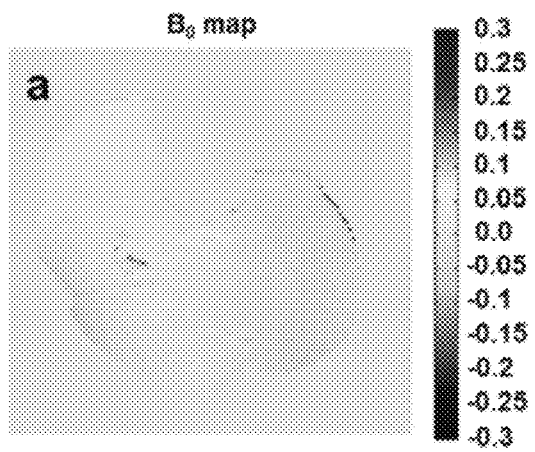
FIG. 6A-FIG. 6E illustrates $B_0$ and $B_1$ correction of in vivo calf muscle CEST and lymphoma tumors in mice.
Figure 6B:
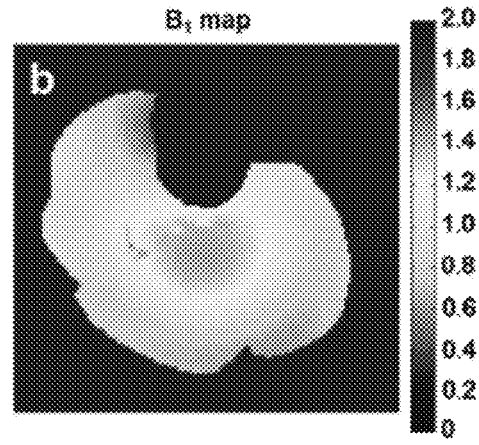
Figure 6C:
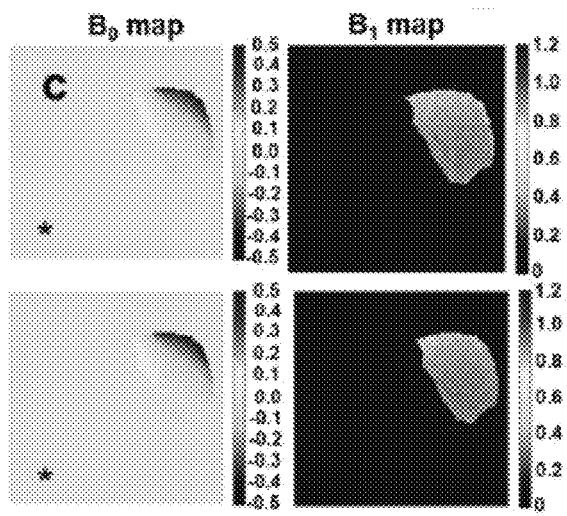
Figure 6D:
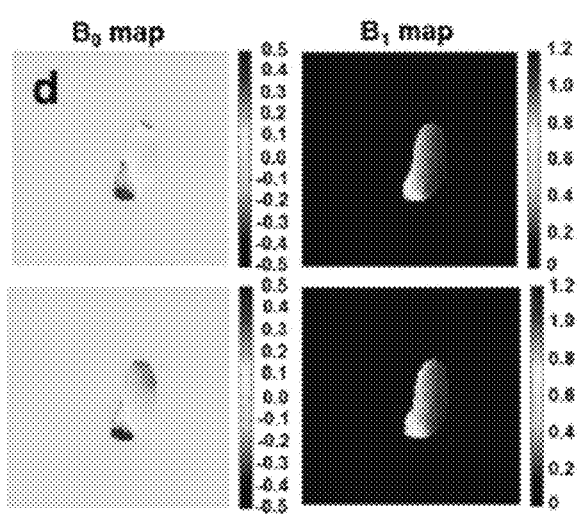
Figure 6E:
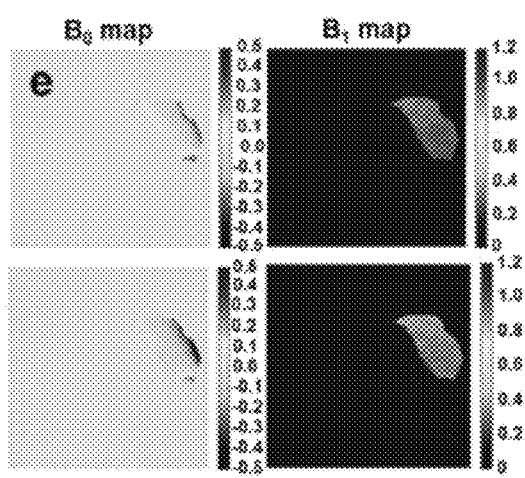

Healthy human calf muscle (FIG. 4A) exhibited an average resting-state LATEST asymmetry of 1.5% (FIG. 4B). This is consistent with the expected low concentration of endogenous lactate in muscle under resting conditions. It also indicates that, with the experimental parameters used, contributions from any other endogenous metabolites to LATEST are negligibly small. However, in the first LATEST image, acquired 3 minutes after cessation of exercise, LATEST asymmetry increased in exercising muscle (gastrocnemius muscle, activated through plantar flexion) to ~4-7%, which recovered to baseline over period of 20 minutes (FIG. 4C). The asymmetry plots from the medial and lateral gastrocnemius muscles from the same subject pre-exercise, and immediately post-exercise, are shown in FIGS. 4D and 4E. Similar increase in post-exercise LATEST is consistently observed in five healthy volunteers (FIG. 5A). Lactate concentration derived from SEL-MQC based edited spectra (FIG. 5B) pre- and post-exercise from 3 healthy volunteers exhibits the same trend (FIG. 5C) as the LATEST. The LATEST correlates well ($R^2$=0.97) with lactate spectral area (FIG. 5D). Based on the slope value of ~0.29% per mM of lactate from spectroscopy, the inventors estimate post-exercise muscle lactate levels to be approximately 14-25 mM. These results are consistent with reported lactate concentration increase of ~20 mM measured in muscle biopsy after intense exercise.

Figure 7A:
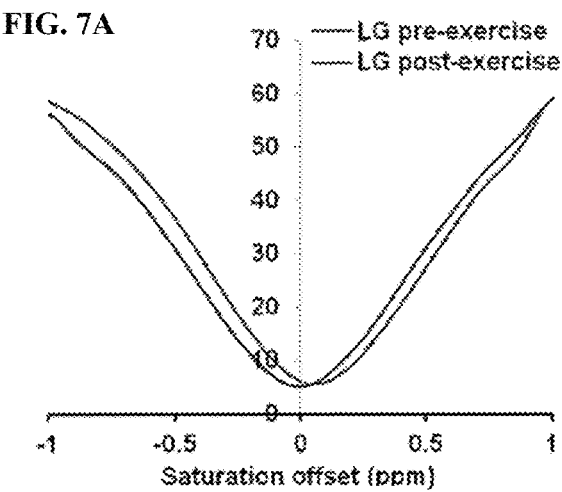
FIG. 7A-FIG. 7C illustrate Z-spectra for human skeletal muscle and animal tumors.
Figure 7B:
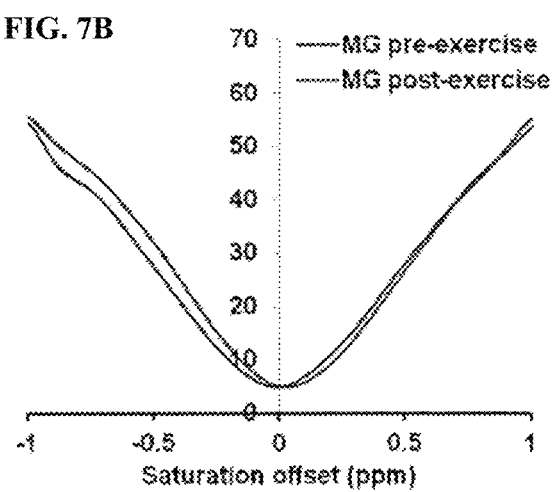
Figure 7C:
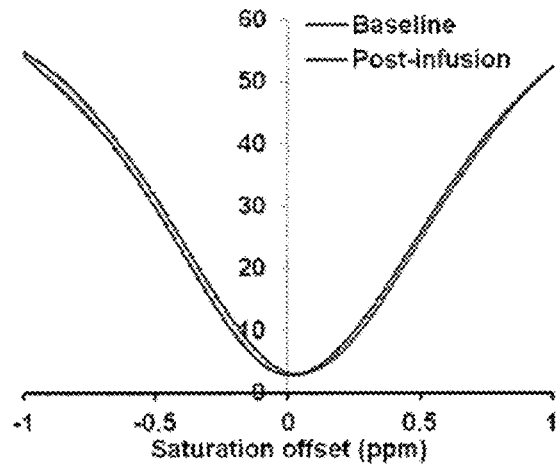

In vivo CEST images, both from human skeletal muscle and from animal tumors, were corrected for $B_0$ and $B_1$ inhomogeneity (FIG. 6). The inventors also included Z-spectra for skeletal muscle and animal tumors in FIG. 7.

Figure 8A:
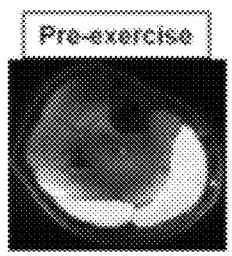
FIG. 8A-FIG. 8C illustrates gastrocnemius muscle $T_2$ measurements.
Figure 8B:
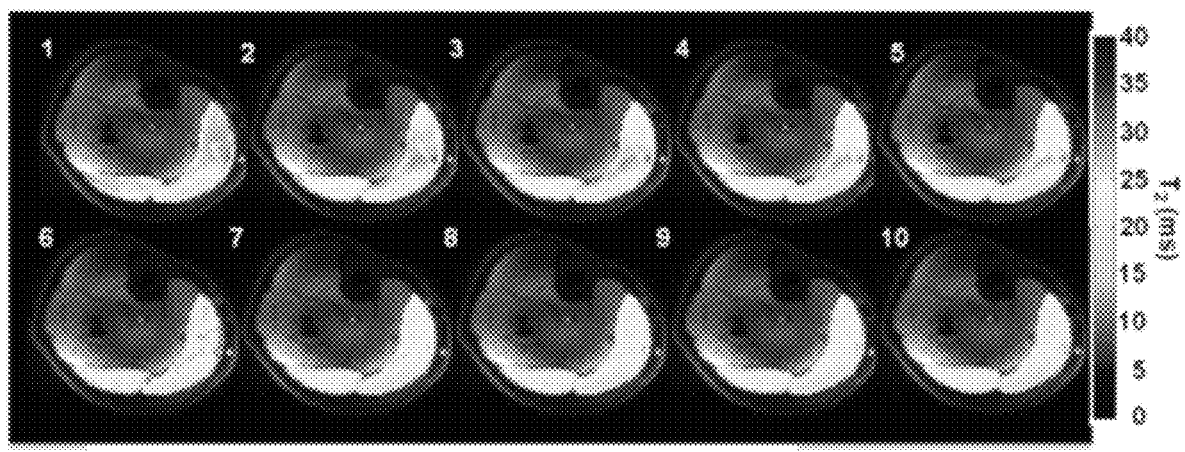
Figure 8C:
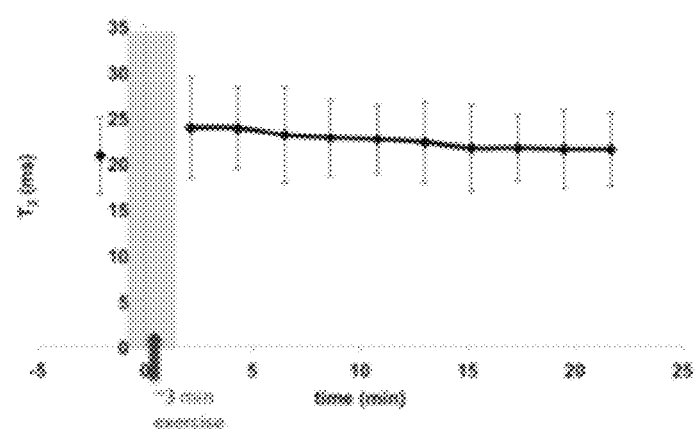

Following intense exercise, the muscle $T_2$ is expected to change, which may confound the LATEST results. To address this issue, the inventors computed $T_2$ maps of skeletal muscle under identical exercising conditions and found that $T_2$ is elevated by <10% immediately after exercise, and stayed constant over 20 minutes (FIG. 8). The inventors estimated that this very small change in the $T_2$ would have a negligible contribution to LATEST.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed is:

1. A magnetic resonance imaging (MM) method comprising:
   (i) applying a lactate-mediated Chemical Exchange Saturation Transfer (CEST) saturation pulse protocol to a patient at a range of frequency offsets around a frequency of exchangeable protons of lactate as well as the same frequency offsets on the opposite side of a water resonance, the lactate-mediated Chemical Exchange Saturation Transfer (CEST) saturation pulse protocol comprising a saturation pulse at a frequency of 0.4 ppm offset from water and a saturation pulse duration and amplitude optimized for lactate-mediated CEST;

(ii) acquiring a magnetic resonance (MR) image of a slice of the body of said patient to which the lactate-mediated CEST saturation pulse protocol has been applied in order to obtain an initial lactate-mediated CEST MRI map;

(iii) administering an effective amount of a contrast agent to said patient, wherein the contrast agent is a metabolic precursor of lactate;

(iv) after administering the effective amount of the contrast agent to said patient, acquiring a second MR image of said slice of the body of said patient to which the lactate-mediated CEST saturation pulse protocol has been applied to obtain a second lactate-mediated CEST MRI map;

(v) determining a lactate-mediated CEST contrast image by taking a ratio of a difference image obtained by subtraction of saturation images obtained in steps (ii) and (iv) with saturation applied at both positive and negative frequencies with respect to water resonance and an image with no saturation; and (vi) displaying the lactate-mediated CEST contrast image as an indication of the level of expression of lactate in said slice of the body of the patient.

2. The magnetic resonance imaging method of claim 1, further comprising adjusting an amplitude and duration of the lactate-mediated CEST saturation pulse protocol based on the rate of exchange of lactate protons.

3. The magnetic resonance imaging method of claim 2, wherein the lactate exchangeable protons are —OH.

4. The magnetic resonance imaging method of claim 1, wherein the lactate-mediated CEST saturation pulse protocol comprises a variable number of pulses with variable shapes including rectangle and Hanning windowed rectangle, variable amplitudes, variable durations, and variable delays.

5. The magnetic resonance imaging method of claim 1, wherein a plurality of lactate-mediated CEST contrast images are determined over a period of time.

6. The magnetic resonance imaging method of claim 5, further comprising displaying the lactate-mediated CEST contrast image as an indication of the level of expression of lactate over time.

7. The magnetic resonance imaging method of claim 1, wherein the contrast agent is administered orally, nasally, intravenously, by infusion, transdermally, or intraperitoneally to the patient.

8. The magnetic resonance imaging method of claim 7, wherein the contrast agent is administered by infusion, and the infusion takes place over a period of time wherein multiple lactate-mediated CEST contrast images may be obtained.

9. The magnetic resonance imaging method of claim 1, further comprising $B_0$ and $B_1$ correction of the saturation images before subtracting the saturation images.

10. The magnetic resonance imaging method of claim 1, further comprising obtaining one or more conventional MM images of said patient.

11. The magnetic resonance imaging method of claim 1, wherein lactate accumulates in abnormal tissue differently than in normal or healthy tissue.

12. The magnetic resonance imaging method of claim 11, wherein the abnormal tissue is neoplastic tissue, inflamed tissue, ischemic tissue, degenerated tissue, or fibrotic tissue.

13. The magnetic resonance imaging method of claim 12, wherein the neoplastic tissue comprises cancerous tissue.

14. The magnetic resonance imaging method of claim 11, wherein the lactate accumulates in abnormal tissue at a different rate than in normal or healthy tissue.

15. The magnetic resonance imaging method of claim 14, wherein the rate of accumulation of lactate in abnormal and normal or healthy tissue is calculated.

16. A method of monitoring the effectiveness of a pharmaceutical agent in treating a condition in a patient, said method comprising:

(i) applying a lactate-mediated Chemical Exchange Saturation Transfer (CEST) saturation pulse protocol to a patient at a range of frequency offsets around a frequency of exchangeable protons of lactate as well as the same frequency offsets on the opposite side of a water resonance, the lactate-mediated Chemical Exchange Saturation Transfer (CEST) saturation pulse protocol incorporating a saturation pulse frequency offset of 0.4 ppm from water;

(ii) acquiring a magnetic resonance (MR) image of a slice of the body of said patient to which the lactate-mediated CEST saturation pulse protocol has been applied in order to obtain an initial lactate-mediated CEST Mill map;

(iii) administering a pharmaceutical agent to said patient;

(iv) administering an effective amount of a contrast agent to said patient, wherein the contrast agent is a metabolic precursor of lactate;

(v) after administering the pharmaceutical agent and the effective amount of the contrast agent to said patient, acquiring a second MR image of said slice of the body of said patient to which the lactate-mediated CEST saturation pulse protocol has been applied to obtain a second lactate-mediated CEST MRI map;

(vi) determining a lactate-mediated CEST contrast image by taking a ratio of a difference image obtained by subtraction of saturation images obtained in steps (ii) and (v) with saturation applied at both positive and negative frequencies with respect to water resonance and an image with no saturation; and (vii) displaying the lactate-mediated CEST contrast image as an indication of the level of expression of lactate.

17. A method of distinguishing abnormal tissue from normal tissue in a patient, said method comprising:

(i) applying to a suspected abnormal tissue a lactate-mediated Chemical Exchange Saturation Transfer (CEST) saturation pulse protocol at a range of frequency offsets around a frequency of exchangeable protons of lactate as well as the same frequency offsets on the opposite side of a water resonance, the lactate-mediated Chemical Exchange Saturation Transfer (CEST) saturation pulse protocol incorporating a saturation frequency offset of 0.4 ppm from water;

(ii) acquiring a magnetic resonance (MR) image of a said suspected abnormal tissue to which the lactate-mediated CEST saturation pulse protocol has been applied in order to obtain an initial lactate-mediated CEST MRI map;

(iii) administering an effective amount of a contrast agent to said patient, wherein the contrast agent is a metabolic precursor of lactate selected from pyruvate, glucose, glutamine, or a combination thereof;

(iv) after administering the effective amount of the contrast agent to said patient, acquiring a second MR image of said suspected abnormal tissue to which the lactate-mediated CEST saturation pulse protocol has been applied to obtain a second lactate-mediated CEST MRI map of the area of the suspected abnormal tissue;

(v) determining a lactate-mediated CEST contrast image by taking a ratio of a difference image obtained by subtraction of saturation images obtained in steps (ii) and (iv) with saturation applied at both positive and negative frequencies with respect to water resonance and an image with no saturation; and (vi) displaying the lactate-mediated CEST contrast image as an indication of the level of expression of lactate.

\* \* \* \* \*

UNITED STATES PATENT AND TRADEMARK OFFICE
CERTIFICATE OF CORRECTION

PATENT NO. : 10,901,058 B2
APPLICATION NO. : 15/424344
DATED : January 26, 2021
INVENTOR(S) : Reddy et al.

Page 1 of 1

It is certified that error appears in the above-identified patent and that said Letters Patent is hereby corrected as shown below:

In the Claims

Under Column no. 12, Claim no. 1, Line no. 61, Replace:
"1. A magnetic resonance imaging (MM) method compris"
With:
--1. A magnetic resonance imaging (MRI) method compris--

Under Column no. 13, Claim no. 10, Line no. 63, Replace:
"further comprising obtaining one or more conventional MM"
With:
--further comprising obtaining one or more conventional MRI--

Under Column no. 14, Claim no. 16, Line no. 28, Replace:
"in order to obtain an initial lactate-mediated CEST Mill"
With:
--in order to obtain an initial lactate-mediated CEST MRI--

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*